United States Patent
Wei et al.

(10) Patent No.: US 9,029,167 B2
(45) Date of Patent: May 12, 2015

(54) PREPARATION OF AN OPTICAL PH SENSOR BASED ON FLUORESCEIN AND 1-HEPTANESULFONIC ACID SODIUM CO-INTERCALATED LAYERED DOUBLE HYDROXIDE

(75) Inventors: Min Wei, Beijing (CN); Wenying Shi, Beijing (CN); Jun Lu, Beijing (CN); Xue Duan, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 317 days.

(21) Appl. No.: 13/520,694

(22) PCT Filed: Mar. 12, 2010

(86) PCT No.: PCT/CN2010/000305
§ 371 (c)(1),
(2), (4) Date: Jul. 5, 2012

(87) PCT Pub. No.: WO2011/082505
PCT Pub. Date: Jul. 14, 2011

(65) Prior Publication Data
US 2012/0282706 A1    Nov. 8, 2012

(30) Foreign Application Priority Data
Jan. 7, 2010    (CN) .......................... 2010 1 0033948

(51) Int. Cl.
*G01N 21/76* (2006.01)
*G01N 31/22* (2006.01)

(52) U.S. Cl.
CPC .................................. *G01N 31/221* (2013.01)

(58) Field of Classification Search
None
See application file for complete search history.

(56) References Cited

U.S. PATENT DOCUMENTS
5,607,644 A    3/1997    Olstein et al.

FOREIGN PATENT DOCUMENTS
CN    1792808    6/2006
CN    101504369    8/2009

OTHER PUBLICATIONS

Costantino, et al., "Surface Uptake and Intercalation of Fluorescein Anions into Zn-Al-Hydrotalcite. Photophysical Characterization of Materials Obtained", Langmuir, vol. 16, No. 26, 2000, pp. 10351-10358.
Shi, et al., "Molecular Orientation and Fluorescence Studies on Naphthalene Acetate Intercalated $Zn_2Al$ Layered Double Hydroxide", The Journal of Physical Chemistry C, vol. 112, No. 50, 2008, pp. 19886-19895.
International Search Report of PCT/CN2010/000305 mailed Oct. 21, 2010.

*Primary Examiner* — Robert Xu
(74) *Attorney, Agent, or Firm* — Hamre, Schumann, Mueller & Larson, P.C.

(57) ABSTRACT

This invention relates to the field of preparation technology of optical pH sensor by co-intercalated fluorescein and 1-heptanesulfonic acid sodium into layered double hydroxide. The sensor is composed by conductive materials and the surface LDH films by co-interacted FLU and HES. The synthesis method is: first: synthesis of LDH colloid suspension, subsequently, the FLU and HES co-intercalated LDH colloid solution was prepared following the ion-exchange method, then the thin film of FLU-HES/LDH was spreaded on the surface of the conductive material by electrophoretic deposition, and the oriental pH sensor was synthesized. The advantages of the present invention is: first, the LDH matrix provides chromophore molecules with a confined and stable environment; the novel electrophoretic deposition strategy in this work provides a method for precise control of thickness (ranging from nanometers to micrometers), and the oriental pH sensor show good pH responsive.

5 Claims, 5 Drawing Sheets

PREPARATION OF AN OPTICAL PH SENSOR BASED ON FLUORESCEIN AND 1-HEPTANESULFONIC ACID SODIUM CO-INTERCALATED LAYERED DOUBLE HYDROXIDE

FIELD OF THE INVENTION

The present invention relates to the field of preparation technology of optical pH sensor, in particular, it relates to an optical pH sensor based on fluorescein and 1-heptanesulfonic acid sodium co-intercalated layered double hydroxide.

BACKGROUND

Optical pH sensors have become very popular analytical tools in the past, due to their broad application in marine research, blood measurement, toxicological assay, and biotechnology. Generally, the fluorophore indicators are immobilized in a matrix for the purpose of obtaining optical pH sensors with stable lifetime and signal. Most optical pH indicators are immobilized in a suitable, proton-permeable, sol-gel polymer matrix. However, some inherent demerits of polymers, such as relatively poor thermal or optical stability as well as toxicity, have limited the practical application of pH sensors to date. Therefore, it is essential to search for novel materials to immobilize the fluorophore indicator in order to achieve optical pH sensors with high stability and environmental compatibility.

Recently, considerable interest has been focused on the fabrication of chromophore-inorganic composite materials, since they may show novel functionalities that are not present in the individual components alone. Among inorganic matrices, layered double hydroxides (LDHs) are one type of important layered materials that display a large versatility in terms of their chemical composition and the ability to build up 2D-organized structures, which show great application. The incorporation of chromophores into the layered double hydroxide (LDH) gallery exhibits the following advantages: First, the LDH matrix provides chromophore molecules with a confined and stable environment, which is the most necessary condition for the solid dye device. Second, chromophore aggregation in the LDH matrix is effectively inhibited by host-guest interactions (e.g., electrostatic attraction, hydrogen bonding), and fluorescence quenching is therefore reduced; Third, chromophore molecules immobilized in the LDH matrix exhibit optical and thermal stability, environmental compatibility, and low operational risk; (4) The LDH can be prepared into gel solution, and is more convenience for pH sensor.

Many preparation methods of LDH thin films have been reported, such as solvent evaporation, layer-by-layer technique, and electrophoretic deposition (EPD) method. However, this technique has recently gained in interest compared with the other methods such as their weak adherence and lower thickness, EPD has its own advantage: 1) easily to control the thickness from nano to micrometer; 2) high deposition rate and continuously. 3) it can make the film on any shape substrate; 4) strong adherence to substrates.

SUMMARY

According to the content, this invention is about the preparation of an optical pH sensor based on fluorescein (FLU) and 1-heptanesulfonic acid sodium (HES) co-intercalated layered double hydroxide. The sensor is composed by conductive materials and the surface LDH films by co-interacted FLU and HES. The content is: first: synthesis of LDH colloid suspension, subsequently, the FLU and HES co-intercalated LDH colloid solution was prepared following the ion-exchange method, then the thin film of FLU-HES/LDH film was fabricated by EPD, and the oriental pH sensor was synthesized. The optical pH sensor based on fluorescein and 1-heptanesulfonic acid sodium co-intercalated layered double hydroxide is composed by conductive materials and the surface plated by fluorescein and 1-heptanesulfonic acid sodium co-intercalated layered double hydroxide.

The composition of the fluorescein and 1-heptanesulfonic acid sodium co-intercalated layered double hydroxide is:

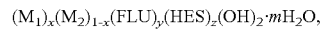

$(M_1)_x(M_2)_{1-x}(FLU)_y(HES)_z(OH)_2 \cdot mH_2O$, $x=0.5-0.8$, $10^{-5} \leq y/z \leq 10^{-2}$, $m$ is the interlayer $H_2O$, and $m=0.3-1.5$.

HES is 1-heptanesulfonic acid sodium; FLU is fluorescein. $M_1$ is any kind of the divalent metal ions of $Mg^{2+}$, $Zn^{2+}$, and $Ni^{2+}$; $M_2$ is any kind of the trivalent metal ions of $Fe^{3+}$, $Al^{3+}$.

The method of preparing the optical pH sensor based on fluorescein and 1-heptanesulfonic acid sodium co-intercalated layered double hydroxide is as following:

a. Soluble $M_1$, $M_2$ metal salt with molar ratio of $M_1/M_2=1\sim 3$ is dissolved in deionized water to form a mixed salt solution with $[M_1]=0.01\sim 1.6$ mol/L; A water solution of $NH_3 \cdot H_2O$ was then added dropwise with stirring until the pH reached a value of 7-10. At this point, the solution changed to a milk-like suspension. The latter was transferred into Teflon-lined Parr reactor and heated for 8-12 h at 110-150° C., then washed by deionized water for 1-6 times; Take 1-10 g milk-like suspension, then dissolved in deionized water 100-200 ml. The colloid suspension was got and tightly stored.

b. fluorescein and 1-heptanesulfonic acid sodium were dissolved in deionized water solvent, and keep the concentration as fluorescein solution $10^{-5}$-$10^{-4}$ mol/l and 1-heptanesulfonic acid sodium solution 0.01-2 mol/l.

c. Get the colloid suspension 5-20 ml of step a, fluorescein solution 1-20 ml of step b, and 1-heptanesulfonic acid sodium solution 1-20 ml, put all above solutions into four-hole boiling flask, and added 100-200 ml deionized water; keep the pH as 7-9 by adding NaOH solution 0.1-1 mol/l. The prepared suspension was agitated under $N_2$ atmosphere for 24-48 h at 20-80° C. Then the suspension was obtained by washing it extensively with water for 1-6 times, as well as ethanol for 1-6 time. Ethanol 100-200 ml was used as a dispersion medium to prepare the colloidal suspension by dispersing the suspension 1-10 g into it.

d. Take steps c colloidal suspension of 1-20 ml, and under ultrasonic sound 2-10 min under $N_2$ atmosphere, using electrophoretic deposition on the conductive material surface by changing the electrophoresis time around 1-60 min, spread on the surface of the conductive material, then vacuum dried 10-50 h under 40-80° C., the optical pH sensor based on fluorescein and 1-heptanesulfonic acid sodium co-intercalated layered double hydroxide was synthesized.

The described $M_1$ is any kind of the divalent metal ions of $Mg^{2+}$, $Zn^{2+}$, and $Ni^{2+}$; $M_2$ is any kind of the trivalent metal ions of $Fe^{3+}$, $Al^{3+}$.

The described conductive material of the pH sensor is one kind of ITO glass, Al, Cu and Ag.

The preferred condition for the present invention is:

a. Soluble magnesium and aluminum salt with molar ratio of $Mg^{2+}/Al^{3+}=2$ is dissolved in deionized water to form a mixed salt solution with $[Mg^{2+}]=1.0$ mol/L; A water solution of $NH_3 \cdot H_2O$ was then added dropwise with stirring until the pH reached a value of 8.5. At this point, a precipitation of Mg/Al hydroxides took place and the solution changed to a milk-like suspension. The latter was transferred into Teflon-lined Parr reactor and heated for 10 h at 140° C., then washed by deionized water for 4 times; Take 5 g milk-like suspension, then dissolved in 150 deionized water. The colloid suspension was got and tightly stored.

b. fluorescein and 1-heptanesulfonic acid sodium were dissolved in deionized water solvent, and keep the concentration as fluorescein solution $2 \times 10^{-5}$ mol/l and 1-heptanesulfonic acid sodium solution 0.02 mol/l.

c. Get the colloid suspension 15 ml of step a, fluorescein solution 10 ml of step b, and 1-heptanesulfonic acid sodium solution 10 ml, put all above solutions into four-hole boiling flask, and added 150 ml deionized water; keep the pH as 8 by adding 0.2 mol/l NaOH solution. The prepared suspension was agitated under $N_2$ atmosphere for 48 h at 65° C. Then the suspension was obtained by washing it extensively with water for 4 times, as well as ethanol for 2 time. Ethanol 100-200 ml was used as a dispersion medium to prepare the colloidal suspension by dispersing the colloid suspension 2 g into it.

d. Take steps c colloidal suspension of 20 ml, and under ultrasonic sound 10 min under nitrogen atmosphere, using electrophoretic deposition on the ITO glass surface, 10 min electrophoresis, spread on the surface of the ITO glass, then vacuum dried 12 h under 65° C., the optical pH sensor based on fluorescein and 1-heptanesulfonic acid sodium co-intercalated layered double hydroxide was synthesized.

The optical pH sensor based on fluorescein and 1-heptanesulfonic acid sodium co-intercalated layered double hydroxide from step d was characterized as following:

(1) XRD and SEM give the evidence that the fluorescein and 1-heptanesulfonic acid have been successfully intercalated into LDH, and the film shows a highly ordered stacking of the c-plane of LDH platelets vertical to the substrate.

(2) The elemental analysis gives the chemical composite of the fluorescein and 1-heptanesulfonic acid sodium co-intercalated layered double hydroxide.

(3) The photostability of the pH sensor was tested by Xe light for 0-7 h.

(4) The fluorescence intensity of the optical pH sensor was recorded under different pH solution (1-14).

The advantages of the present invention is: First, the LDH matrix provides chromophore molecules with a confined and stable environment; the novel EPD strategy in this work not only provides a method for fabrication of highly oriented luminescence films with precise control of thickness (ranging from nanometers to micrometers), but also low cost, high deposition rate, can be formed on any substrates, and strong adherence to substrates; the oriental pH sensor show good pH responsive.

DETAILED DESCRIPTION

Example 1

Figure 1:
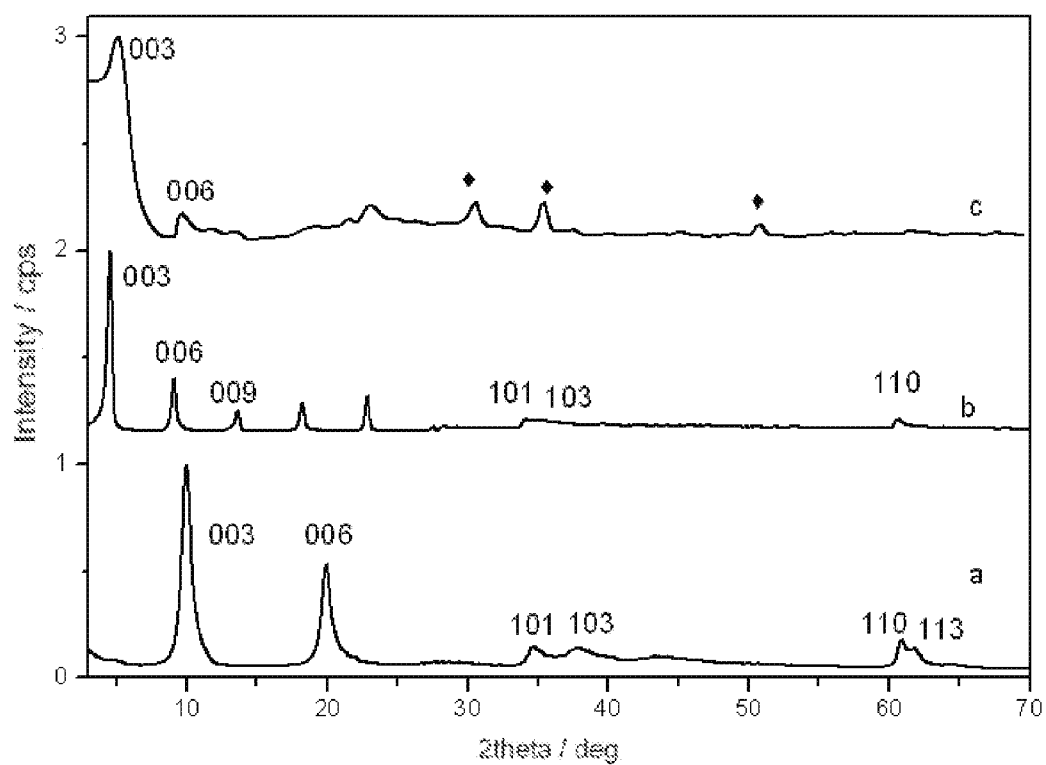
FIG. 1: XRD patterns of the optical pH sensor based on fluorescein and 1-heptanesulfonic acid sodium co-intercalated layered double hydroxide synthesized by example 1. Abscissa is 2θ, unit: degree; the vertical axis is its intensity; a: $Mg_2Al$—$NO_3$ LDH; b: powder samples for fluorescein and 1-heptanesulfonic acid sodium co-intercalated layered double hydroxide; c: XRD patterns for the fluorescein and 1-heptanesulfonic acid sodium co-intercalated layered double hydroxide thin-film samples. "♦" denotes reflections from the ITO substrate.

Step A: The soluble $Mg(NO_3)_2 \cdot 6H_2O$ (15.38 g), $Al(NO_3)_3 \cdot 9H_2O$ (11.25 g) metal salt with molar ratio of Mg/Al=2 was dissolved in deionized water to form a mixed salt solution, $NH_3 \cdot H_2O$ solution (45 ml) was then added dropwise with stirring until the pH reached a value of 8.5. At this point, a milk-like suspension was got. The latter was transferred into Teflon-lined Parr reactor and heated for 10 h at 140° C., then washed by deionized water for 4 times; Take 2 g milk-like suspension, then dissolved in deionized water (150 ml). The colloid Suspension was got and tightly stored.

Step B: FLU and HES were dissolved in deionized water solvent respectively, and keep the concentration as FLU solution ($2\times10^{-5}$ mol/l) and HES solution (0.01 mol/l).

Step C: Get the step A colloid Suspension (15 ml); step B FLU solution (10 ml), and HES solution (10 ml), put all above solutions into four-hole boiling flask, and added 150 ml deionized water; keep the pH as 8 by adding NaOH solution 0.2 mol/l. The prepared suspension was agitated under $N_2$ atmosphere for 48 h at 65° C. Then the colloid suspension was obtained by washing it extensively with water for 4 times, as well as ethanol for 2 time. Ethanol (150 ml) was used as a dispersion medium to prepare the colloidal suspension by dispersing the colloid suspension (2 g) into it, and then the colloid suspension was got and tightly stored.

Step D: Take steps C colloid suspension of 20 ml, and under ultrasonic sound 5 min under nitrogen atmosphere, using electrophoretic deposition on the ITO glass surface, 3 min electrophoresis, spread on the surface of the ITO glass, then the film was vacuum dried 12 h under 65° C., the optical pH sensor based on fluorescein and 1-heptanesulfonic acid sodium co-intercalated layered double hydroxide was synthesized.

The fluorescence intensity of the pH sensor from step D was recorded under different pH solution (4.01, 5.02, 5.51, 5.98, 6.51, 6.62, 6.71, 6.85, 7.02, 8.01, 10.01, 11.02, 12.0).

Figure 2:
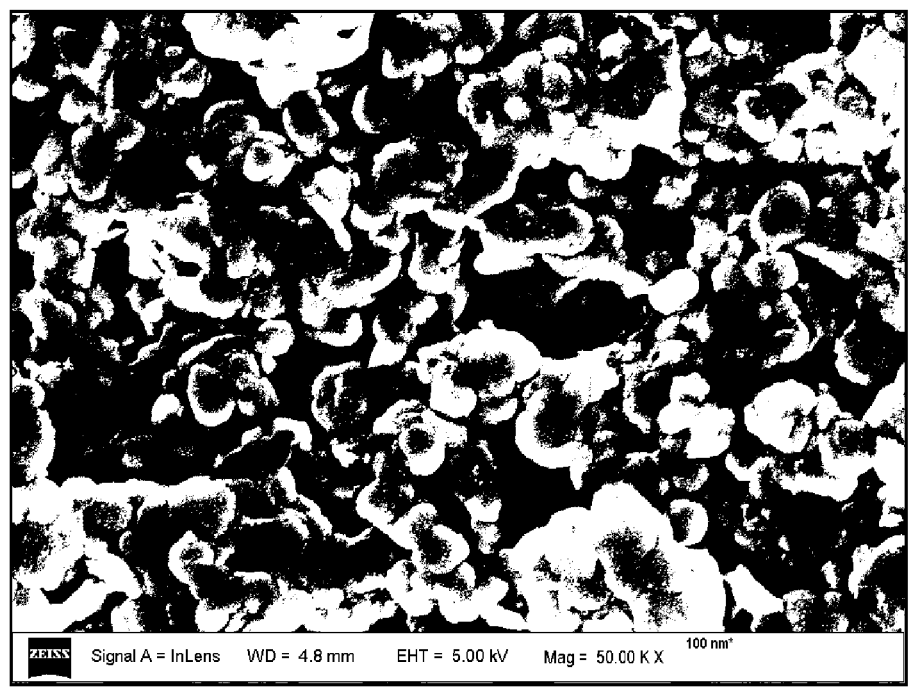
FIG. 2 is the SEM images of the optical pH sensor based on fluorescein and 1-heptanesulfonic acid sodium co-intercalated layered double hydroxide synthesized by example 1.
Figure 3:
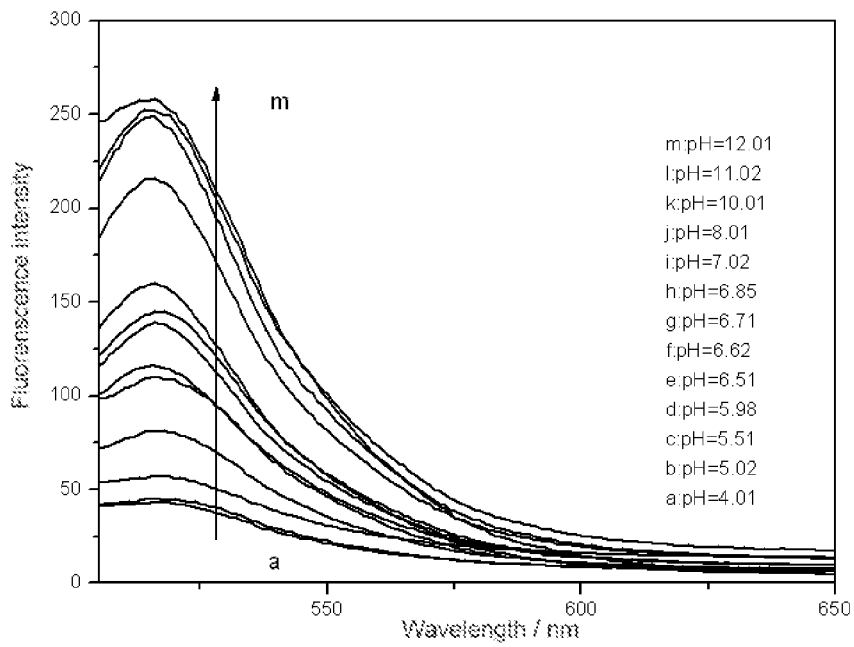
FIG. 3: Emission spectra of the optical pH sensor based on fluorescein and 1-heptanesulfonic acid sodium co-intercalated layered double hydroxide synthesized by example 1 at different pH values (4.01, 5.02, 5.51, 5.98, 6.51, 6.62, 6.71, 6.85, 7.02, 8.01, 10.01, 11.02 and 12.01) Abscissa: wavelength, unit: nm; vertical axis: intensity.
Figure 4:
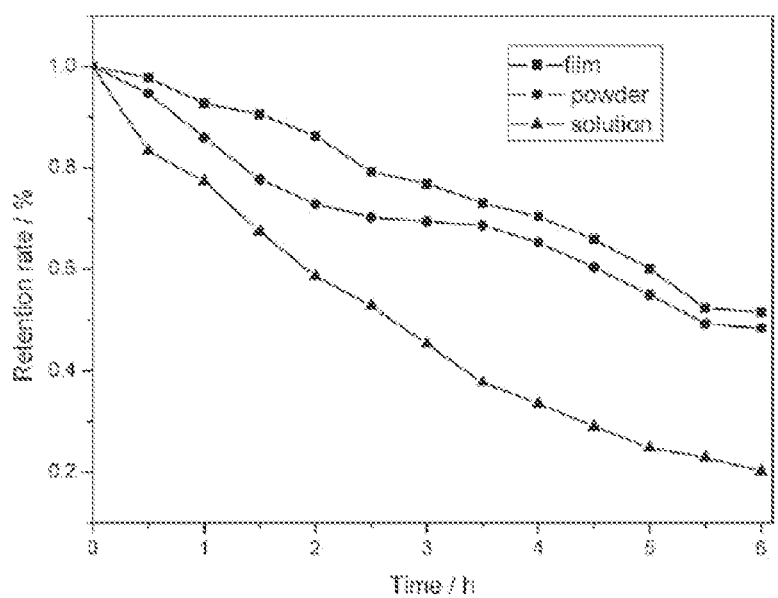
FIG. 4: The photostability of the fluorescein solution, the powder and the thin film of the fluorescein and 1-heptanesulfonic acid sodium co-intercalated layered double hydroxide synthesized by example 1, and as a function of bleaching time (0, 0.5, 1, 1.5, 2, 2.5, 3, 3.5, 4, 4.5, 5, 5.5 and 6 h). Abscissa: time, unit: h; vertical axis: intensity.
Figure 5:
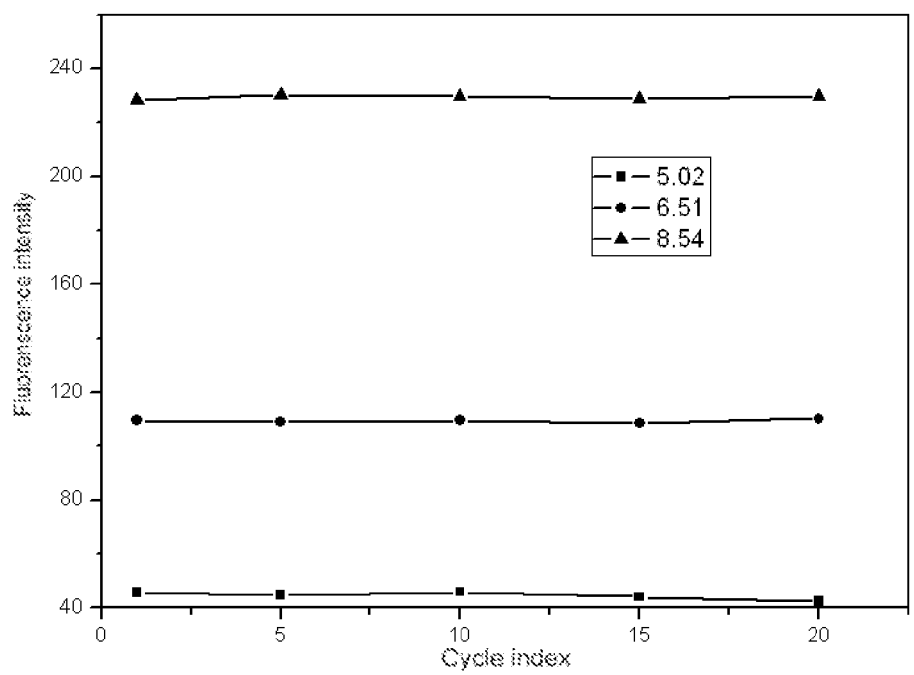
FIG. 5: Fluorescence intensity of the optical pH sensor based on fluorescein and 1-heptanesulfonic acid sodium co-intercalated layered double hydroxide synthesized by example 1 recorded after 1-20 cycles at pH 5.02, 6.51, and 8.54. Abscissa: operation cycle s; vertical axis: the PL intensity in 516 nm.

As shown in FIG. 1, the 003 reflection of the FLU and HES co-intercalated LDH sample at 2θ=4.82° shows an interlayer distance of 1.82 nm, while the interlayer distance of MgAl-LDH is 0.87, indicating that FLU and HES were co-intercalated into the galleries of the LDH. From FIG. 1, it can be seen that the FLU and HES co-intercalated LDH thin films show the disappearance of (1 0 1) and (1 1 1) reflections, indicating a highly ordered stacking of the ab plane of LDH platelets parallel to the substrate. SEM of the film (FIG. 2B) demonstrates that the FLU and HES co-intercalated LDH nanoplatelets are densely packed on the substrate plane with good c-orientation; The chemical composite of the FLU and HES co-intercalated LDH is $[Mg_{0.67}Al_{0.33}(OH)_2](FLU)_{0.001}(HES)_{0.329}.0.51H_2O$ as shown in ICP. FIG. 3 shows that the fluorescence intensity of the FLU and HES co-intercalated LDH thin film increases as the pH value, indicate that the good responsive of the pH sensors. FIG. 4 show that the FLU and HES co-intercalated LDH film show the improving photostability that the powder and FLU significantly. The recycle experiment of the LDH films show that no obvious signal drift was observed, and the good repeatability was obtained with RSD of 1.35% (pH 5.02), 0.65% (pH 6.51), and 0.84% (pH 8.54).

Figure 6:
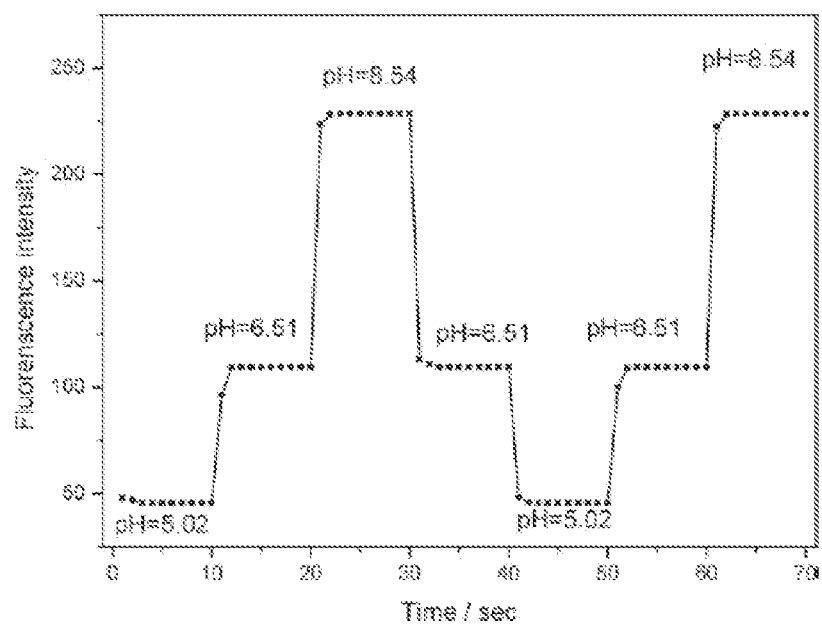
FIG. 6: Response time of the optical pH sensor based on fluorescein and 1-heptanesulfonic acid sodium co-intercalated layered double hydroxide synthesized by example 1 recorded by fluorescence intensity at the maximum emission peak in pH 5.02, 6.51, 8.54. Abscissa: time; unit: second; Vertical axis: the PL intensity in 516 nm.

FIG. 6 show that the Response time of the FLU and HES co-intercalated LDH pH sensor recorded by fluorescence intensity is very quick, with only 2 seconds.

Sample 2

Step A: The soluble $Mg(NO_3)_2.6H_2O$ (23.04 g), $Al(NO_3)_3.9H_2O$ (11.25 g) metal salt with molar ratio of Mg/Al=3 was dissolved in deionized water (150 ml) to form a mixed salt solution, $NH_3.H_2O$ solution (45 ml) was then added dropwise with stirring until the pH reached a value of 8.0. At this point, a milk-like suspension was got; The latter was transferred into Teflon-lined Parr reactor and heated for 10 h at 130° C., then washed by deionized water for 3 times; Take 3 g milk-like suspension, then dissolved in deionized water (160 ml). The colloid suspension was got and tightly stored.

Step B: FLU and HES were dissolved in deionized water solvent, and keep the concentration as FLU solution ($2\times10^{-5}$ mol/l) and HES solution (0.01 mol/l).

Step C: Get the step A colloid suspension (20 ml); step B: FLU solution (15 ml), and HES solution (15 ml), put all above solutions into four-hole boiling flask, and added 150 ml deionized water; keep the pH as 8 by adding NaOH solution 0.2 mol/l. The prepared suspension was agitated under $N_2$ atmosphere for 48 h at 65° C. Then the colloid suspension was obtained by washing it extensively with water for 5 times, as well as ethanol for 3 time. Ethanol was used as a dispersion medium to prepare the colloidal suspension by dispersing the colloid suspension (3 g) into it, then the colloid suspension was got and tightly stored.

Step D: Take steps C colloid suspension of 10 ml, and under ultrasonic sound 5 min under nitrogen atmosphere, using electrophoretic deposition on the ITO glass surface, 10 min electrophoresis, spread on the surface of the ITO glass, then the film was vacuum dried 10 h under 30° C., the optical pH sensor based on fluorescein and 1-heptanesulfonic acid sodium co-intercalated layered double hydroxide was synthesized.

The fluorescence intensity of the pH sensor from step D was recorded under different pH solution (4.01, 5.02, 5.51, 5.98, 6.51, 6.62, 6.71, 6.85, 7.02, 8.01, 10.01, 11.02, 12.0).

Figure 7:
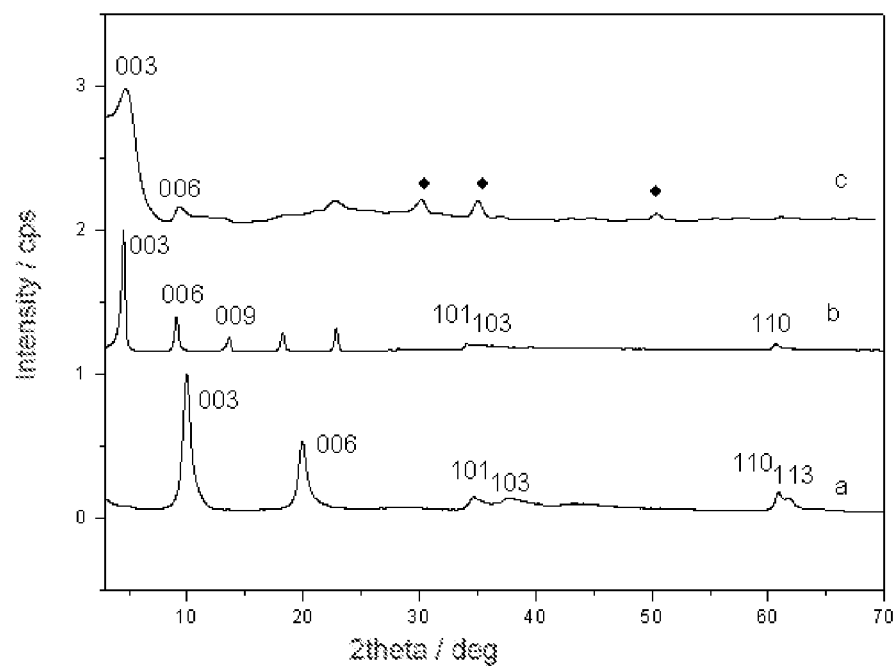
FIG. 7: XRD patterns of the optical pH sensor based on fluorescein and 1-heptanesulfonic acid sodium co-intercalated layered double hydroxide synthesized by example 2. Abscissa is 2θ, unit: degree; the vertical axis is its intensity; a: $Mg_3Al$—$NO_3$ LDH; b: powder samples for fluorescein and 1-heptanesulfonic acid sodium co-intercalated layered double hydroxide; c: XRD patterns for the fluorescein and 1-heptanesulfonic acid sodium co-intercalated layered double hydroxide thin-film samples. "♦" denotes reflections from the ITO substrate.

As shown in FIG. 7, the 003 reflection of the FLU and HES co-intercalated LDH sample at 2θ=4.72° shows an interlayer distance of 1.87 nm, while the interlayer distance of MgAl-LDH is 0.87, indicating that FLU and HES were co-intercalated into the galleries of the LDH. From FIG. 1, it can be seen that the FLU and HES co-intercalated LDH thin films show the disappearance of (1 0 1) and (1 1 1) reflections, indicating a highly ordered stacking of the ab plane of LDH platelets parallel to the substrate. SEM of the film demonstrates that the FLU and HES co-intercalated LDH nanoplatelets are densely packed on the substrate plane with good c-orientation; the chemical composite of the FLU and HES co-intercalated LDH is $[Mg_{0.75}Al_{0.25}(OH)_2](FLU)_{0.001}(HES)_{0.329}.0.45H_2O$ as shown in ICP. The fluorescence intensity of the FLU and HES co-intercalated LDH thin film increases as the pH value, indicate that the good responsive of the pH sensors. The FLU and HES co-intercalated LDH film show the improving photostability that the powder and FLU significantly. The recycle experiment of the LDH films show that no obvious signal drift was observed, and the good repeatability was obtained with RSD of 1.45% (pH 5.51), 0.85% (pH 7.02), and 0.94% (pH 10.01), shows that the response time of the FLU and HES co-intercalated LDH pH sensor recorded by fluorescence intensity is very quick, with only 2 seconds.

Sample 3

Step A: The soluble $Zn(NO_3)_2.6H_2O$ (17.64 g), $Al(NO_3)_3.9H_2O$ (11.25 g) metal salt with molar ratio of Zn/Al=2 was dissolved in deionized water to form a mixed salt solution, $NH_3.H_2O$ solution (45 ml) was then added dropwise with stirring until the pH reached a value of 7. At this point, a milk-like suspension was got; The latter was transferred into Teflon-lined Parr reactor and heated for 10 h at 120° C., then washed by deionized water for 3 times; Take 3 g milk-like suspension, then dissolved in deionized water (160 ml). The colloid suspension was got and tightly stored.

Step B: FLU and HES were dissolved in deionized water solvent, and keep the concentration as FLU solution ($5\times10^{-5}$ mol/l) and HES solution (0.02 mol/l).

Step C: Get the step A colloid suspension (16 ml); step B: FLU solution (8 ml), and HES solution (8 ml), put all above solutions into four-hole boiling flask, and added 150 ml deionized water; keep the pH as 8 by adding NaOH solution 0.2 mol/l. The prepared suspension was agitated under $N_2$ atmosphere for 48 h at 65° C. Then the colloid suspension was obtained by washing it extensively with water for 3 times, as well as ethanol for 3 time. Ethanol (150 ml) was used as a dispersion medium to prepare the colloidal suspension by dispersing the colloid suspension (3 g) into it, then the colloid suspension was got and tightly stored Step D: Take steps C colloid suspension of 16 ml, and under ultrasonic sound 6 min under nitrogen atmosphere, using electrophoretic deposition on the ITO glass surface, 5 min electrophoresis, spread on the surface of the ITO glass, then the film was vacuum dried 13 h under 65° C., the optical pH sensor based on fluorescein and 1-heptanesulfonic acid sodium co-intercalated layered double hydroxide was synthesized.

The fluorescence intensity of the pH sensor from step D was recorded under different pH solution (4.01, 5.02, 5.51, 5.98, 6.51, 6.62, 6.71, 6.85, 7.02, 8.01, 10.01, 11.02, 12.0).

Figure 8:
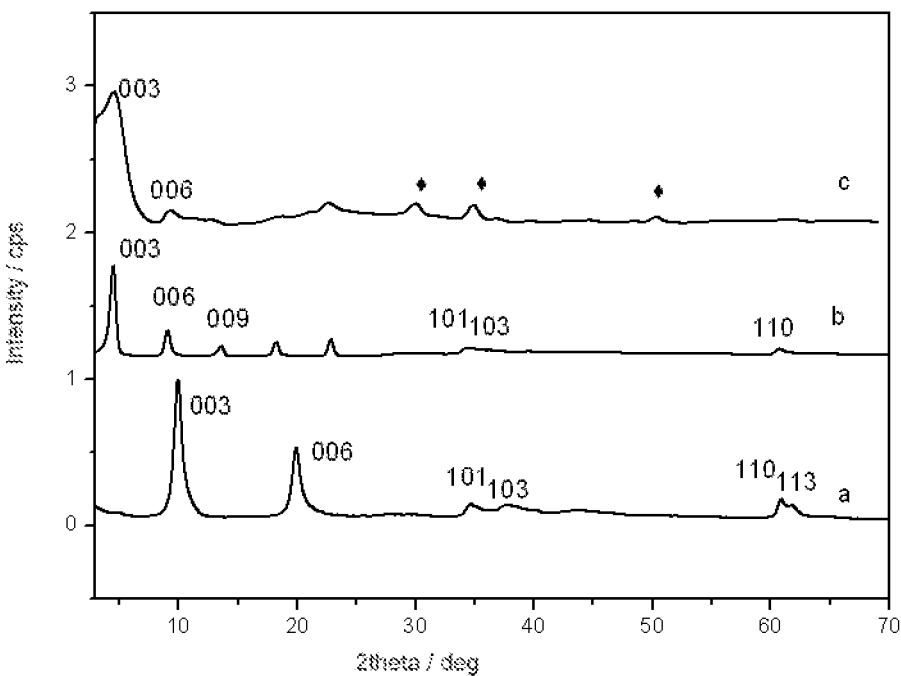
FIG. 8: XRD patterns of the optical pH sensor based on fluorescein and 1-heptanesulfonic acid sodium co-intercalated layered double hydroxide synthesized by example 3. Abscissa is 2θ, unit: degree; the vertical axis is its intensity; a: $Zn_2Al$—$NO_3$ LDH; b: powder samples for fluorescein and 1-heptanesulfonic acid sodium co-intercalated layered double hydroxide; c: XRD patterns for the fluorescein and 1-heptanesulfonic acid sodium co-intercalated layered double hydroxide thin-film samples. "♦" denotes reflections from the ITO substrate.

As shown in FIG. 8, the 003 reflection of the FLU and HES co-intercalated LDH sample at $2\theta=4.60°$ shows an interlayer distance of 1.90 nm, while the interlayer distance of MgAl-LDH is 0.87, indicating that FLU and HES were co-intercalated into the galleries of the LDH. From FIG. 1, it can be seen that the FLU and HES co-intercalated LDH thin films show the disappearance of (1 0 1) and (1 1 1) reflections, indicating a highly ordered stacking of the ab plane of LDH platelets parallel to the substrate. SEM of the film demonstrates that the FLU and HES co-intercalated LDH nanoplatelets are densely packed on the substrate plane with good c-orientation; The chemical composite of the FLU and HES co-intercalated LDH is $[Zn_{0.67}Al_{0.33}(OH)_2](FLU)_{0.001}(HES)_{0.329} \cdot 0.32H_2O$ as shown in ICP. The fluorescence intensity of the FLU and HES co-intercalated LDH thin film increases as the pH value, indicate that the good responsive of the pH sensors. The FLU and HES co-intercalated LDH film show the improving photostability that the powder and FLU significantly. The recycle experiment of the LDH films show that no obvious signal drift was observed, and good repeatability was obtained with RSD of 1.25% (pH 5.51), 0.75% (pH 7.02), and 0.96% (pH 10.01). The response time of the FLU and HES co-intercalated LDH pH sensor recorded by fluorescence intensity is very quick, with only 2 seconds.

Sample 4

Step A: The soluble $Zn(NO_3)_2 \cdot 6H_2O$ (17.82 g), $Al(NO_3)_3 \cdot 9H_2O$ (11.25 g) metal salt with molar ratio of Zn/Al=3 was dissolved in deionized water to form a mixed salt solution, $NH_3 \cdot H_2O$ solution (45 ml) was then added dropwise with stirring until the pH reached a value of 7.5. At this point, a milk-like suspension was got; The latter was transferred into Teflon-lined Parr reactor and heated for 11 h at 130° C., then washed by deionized water for 5 times; take 1 g milk-like suspension, then dissolved in deionized water (170 ml). The colloid Suspension was got and tightly stored.

Step B: FLU and HES were dissolved in deionized water solvent, and keep the concentration as FLU solution ($2 \times 10^{-5}$ mol/l) and HES solution (0.2 mol/l).

Step C: Get the step A colloid Suspension (11 ml); step B: FLU solution (5 ml), and HES solution (5 ml), put all above solutions into four-hole boiling flask, and added 160 ml deionized water; keep the pH as 8.0 by adding NaOH solution 0.2 mol/l. The prepared suspension was agitated under $N_2$ atmosphere for 48 h at 65° C. Then the colloid suspension was obtained by washing it extensively with water for 3 times, as well as ethanol for 3 time. Ethanol (150 ml) was used as a dispersion medium to prepare the colloidal suspension by dispersing the colloid suspension (1 g) into it, and then the colloid suspension was got and tightly stored Step D: Take steps C colloid suspension of 16 ml, and under ultrasonic sound 6 min under nitrogen atmosphere, using electrophoretic deposition on the ITO glass surface, 7 min electrophoresis, spread on the surface of the ITO glass, then the film was vacuum dried 11 h under 60° C., the optical pH sensor based on fluorescein and 1-heptanesulfonic acid sodium co-intercalated layered double hydroxide was synthesized.

The fluorescence intensity of the pH sensor from step D was recorded under different pH solution (4.01, 5.02, 5.51, 5.98, 6.51, 6.62, 6.71, 6.85, 7.02, 8.01, 10.01, 11.02, 12.0).

Figure 9:
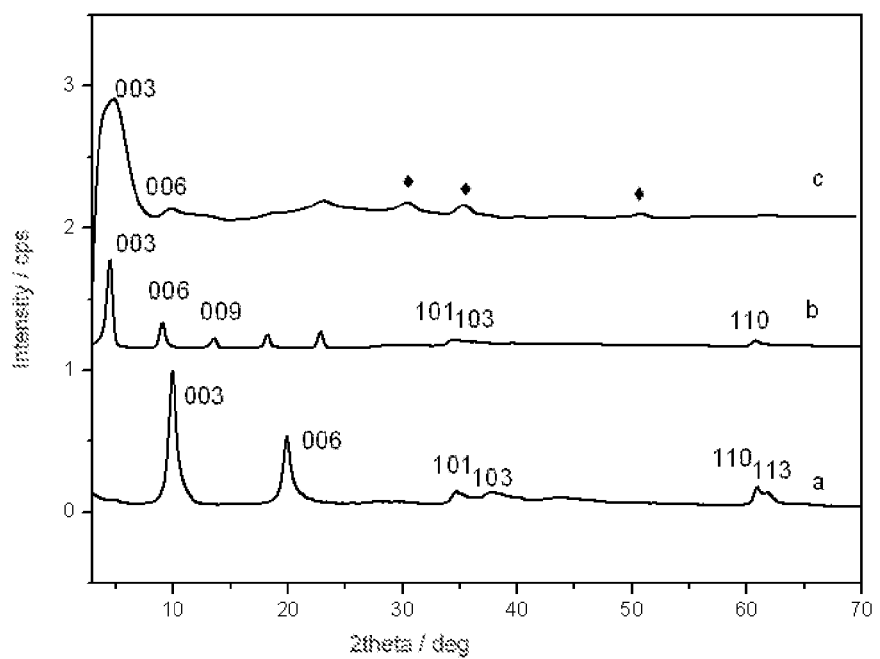
FIG. 9: XRD patterns of the optical pH sensor based on fluorescein and 1-heptanesulfonic acid sodium co-intercalated layered double hydroxide synthesized by example 4. Abscissa is 2θ, unit: degree; the vertical axis is its intensity; a: $Zn_3Al$—$NO_3$ LDH; b: powder samples for fluorescein and 1-heptanesulfonic acid sodium co-intercalated layered double hydroxide; c: XRD patterns for the fluorescein and 1-heptanesulfonic acid sodium co-intercalated layered double hydroxide thin-film samples. "♦" denotes reflections from the ITO substrate.

As shown in FIG. 9, the 003 reflection of the FLU and HES co-intercalated LDH sample at $2\theta=4.92°$ shows an interlayer distance of 1.95 nm, while the interlayer distance of MgAl-LDH is 0.87, indicating that FLU and HES were co-intercalated into the galleries of the LDH. From FIG. 1, it can be seen that the FLU and HES co-intercalated LDH thin films show the disappearance of (1 0 1) and (1 1 1) reflections, indicating a highly ordered stacking of the ab plane of LDH platelets parallel to the substrate. SEM of the film demonstrates that the FLU and HES co-intercalated LDH nanoplatelets are densely packed on the substrate plane with good c-orientation; The chemical composite of the FLU and HES co-intercalated LDH is $[Zn_{0.75}Al_{0.25}(OH)_2](FLU)_{0.0001}(HES)_{0.3299} \cdot 0.68H_2O$ as shown in ICP. The fluorescence intensity of the FLU and HES co-intercalated LDH thin film increases as the pH value, indicate that the good responsive of the pH sensors. The FLU and HES co-intercalated LDH film show the improving photostability that the powder and FLU significantly. The recycle experiment of the LDH films show that no obvious signal drift was observed, and good repeatability was obtained with RSD of 1.43% (pH 5.51), 0.96% (pH 7.02), and 0.94% (pH 10.01). The response time of the FLU and HES co-intercalated LDH pH sensor recorded by fluorescence intensity is very quick, with only 2 seconds.

The invention claimed is:

1. An optical pH sensor based on fluorescein and 1-heptanesulfonic acid sodium co-intercalated layered double hydroxide, wherein the sensor is composed by a conductive material and a surface plated by a composition of fluorescein and 1-heptanesulfonic acid sodium co-intercalated layered double hydroxide, the composition of the fluorescein and 1-heptanesulfonic acid sodium co-intercalated layered double hydroxide having the formula:

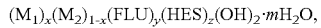

$(M_1)_x(M_2)_{1-x}(FLU)_y(HES)_z(OH)_2 \cdot mH_2O$, wherein x=0.5-0.8, $10^{-5} \leq y/z \leq 10^{-2}$, m is the interlayer $H_2O$, m=0.3-1.5, HES is 1-heptanesulfonic acid sodium, FLU is fluorescein, $M_1$ is a divalent metal ion selected from $Mg^{2+}$, $Zn^{2+}$, and $Ni^{2+}$, and $M_2$ is a trivalent metal ion selected from $Fe^{3+}$ and $Al^{3+}$.

2. A method of preparing an optical pH sensor based on fluorescein and 1-heptanesulfonic acid sodium co-intercalated layered double hydroxide, comprising:

a. dissolving soluble $M_1$, $M_2$ metal salt with a molar ratio of $M_1/M_2=1\sim3$ in deionized water to form a mixed salt solution with $[M_1]=0.01\sim1.6$ mol/L, adding a water solution of $NH_3 \cdot H_2O$ to the mixed salt solution dropwise with stirring until the pH reached a value of 7-10 to obtain a milk-like suspension, transferring the milk-like suspension into a Teflon-lined Parr reactor and heating for 8-12 h at 110-150° C., washing with deionized water 1-6 times; dissolving 1-10 g of the milk-like suspension in 100-200 ml deionized water to obtain a colloid suspension;

b. dissolving fluorescein and 1-heptanesulfonic acid sodium in deionized water solvent to obtain a concentration of fluorescein solution at $10^{-5}$-$10^{-4}$ mol/l and a concentration of 1-heptanesulfonic acid sodium solution at 0.01-2 mol/l;

c. putting 5-20 ml of the colloid suspension of step a, 1-20 ml of the fluorescein solution of step b, and 1-20 ml of 1-heptanesulfonic acid sodium solution of step b into a four-hole boiling flask, adding 100-200 ml deionized water, maintaining the pH at 7-9 by adding a NaOH solution at 0.1-1 mol/l to obtain a suspension, agitating the suspension under an $N_2$ atmosphere for 24-48 h at 20-80° C.; washing the suspension with water 1-6 times, and with ethanol 1-6 times, dispersing 1-10 g of the suspension into 100-200 ml of ethanol to obtain a colloidal suspension d. putting 1-20 ml of the colloidal suspension of step c, under ultrasonic sound for 2-10 min under an $N_2$ atmosphere, using electrophoretic deposition on a surface of a conductive material by changing an electrophoresis time around 1-60 min, spreading on the surface of the conductive material, drying under vacuum for 10-50 h under 40-80° C. to synthesize the optical pH sensor based on fluorescein and 1-heptanesulfonic acid sodium co-intercalated layered double hydroxide wherein $M_1$ is a divalent metal ion selected from $Mg^{2+}$, $Zn^{2+}$, and $Ni^{2+}$, and $M_2$ is a trivalent metal ion selected from $Fe^{3+}$ and $Al^{3+}$.

3. The optical pH sensor according to the claim 1, wherein the conductive material of the pH sensor is one of an ITO glass, Al, Cu and Ag.

4. The method according to the claim 2, wherein the conductive material of the pH sensor is one of an ITO glass, Al, Cu and Ag.

5. A method of preparing an optical pH sensor based on fluorescein and 1-heptanesulfonic acid sodium co-intercalated layered double hydroxide, comprising:

a. dissolving soluble magnesium and aluminum salt with a molar ratio of $Mg^{2+}/Al^{3+}=2$ in deionized water to form a mixed salt solution with $[Mg^{2+}]=1.0$ mol/L, adding a water solution of $NH_3.H_2O$ to the mixed salt solution dropwise with stirring until the pH reached a value of 8.5, precipitating Mg/Al hydroxides to obtain a milk-like suspension transferring the milk-like suspension into a Teflon-lined Parr reactor and heating for 10 h at 140° C., washing with deionized water 4 times dissolving 5 g of the milk-like suspension in 150 ml deionized water to obtain a colloid suspension;

b. dissolving fluorescein and 1-heptanesulfonic acid sodium in deionized water solvent to obtain a concentration of fluorescein solution at $2\times10^{-5}$ mol/l and a concentration of 1-heptanesulfonic acid sodium solution at 0.02 mol/l;

c. putting 15 ml of the colloid suspension of step a, 10 ml of the fluorescein solution of step b, and 10 ml of 1-heptanesulfonic acid sodium solution of step b into a four-hole boiling flask, adding 150 ml deionized water; maintaining the pH at 8 by adding 0.2 mol/l of NaOH solution to obtain a suspension, agitating the suspension under an $N_2$ atmosphere for 48 h at 65° C. washing the suspension with water 4 times, and with ethanol 2 times, dispersing 2 g of the suspension into 100-200 ml of ethanol to obtain a colloidal suspension;

d. putting 20 ml of the colloidal suspension of step c under ultrasonic sound for 10 min under a nitrogen atmosphere, using electrophoretic deposition on an ITO glass surface under 10 min of electrophoresis, spreading on the surface of the ITO glass, drying under vacuum for 12 h under 65° C. to synthesize the optical pH sensor based on fluorescein and 1-heptanesulfonic acid sodium co-intercalated layered double hydroxide.

* * * * *